(12) United States Patent
Stewart et al.

(10) Patent No.: US 7,947,282 B2
(45) Date of Patent: *May 24, 2011

(54) METHODS OF TREATMENT USING VASCULAR OCCLUSION IN COMBINATION THERAPIES

(75) Inventors: Michael W. Stewart, Spruce Grove (CA); Antoine Noujaim, Edmonton (CA); Bruce D. Hirsche, legal representative, Edmonton (CA); Roland H. Person, Kelowna (CA)

(73) Assignee: IMBiotechnologies Ltd, Edmonton, AB (CA)

( * ) Notice: Subject to any disclaimer, the term of this patent is extended or adjusted under 35 U.S.C. 154(b) by 910 days.

This patent is subject to a terminal disclaimer.

(21) Appl. No.: 11/464,250

(22) Filed: Aug. 14, 2006

(65) Prior Publication Data

US 2007/0098724 A1    May 3, 2007

Related U.S. Application Data

(63) Continuation-in-part of application No. 10/241,717, filed on Sep. 12, 2002, now Pat. No. 6,960,352, and a continuation-in-part of application No. 10/101,731, filed on Mar. 21, 2002, now abandoned.

(60) Provisional application No. 60/708,757, filed on Aug. 17, 2005.

(51) Int. Cl.
*A61K 39/00* (2006.01)
(52) U.S. Cl. ............... 424/193.1; 424/184.1; 514/13.5; 514/13.8; 514/14.1
(58) Field of Classification Search ............... None
See application file for complete search history.

(56) References Cited

U.S. PATENT DOCUMENTS 6,960,352 B2 * 11/2005 Noujaim et al. ............ 424/423

FOREIGN PATENT DOCUMENTS

WO    WO 0029029 A1 *  5/2000

OTHER PUBLICATIONS

Merck Manual: Seventeenth Edition (1999). Beers and Berkow, Eds. Merck Research Laboratories, Whitehouse Station, NJ. pp. 918-920.*
Anderson, Peptides. Mar. 2003;24(3):487-501.*
Mannel et al., Mol Pathol. Aug. 1997;50(4):175-85.*
McCaffery et al., Blood. Jun. 1986;67(6):1757-64.*
Limb, et al., Platelet expression of tumour necrosis factor-alpha (TNF-a), TNF receptors and intercellular adhesion molecule-1 (ICAM-1) in patients with proliferative diabetic retinopathy, Clinical and Experimental Immunology, 1999, 213-218, 118.
Grunkemeier, et al., The effect of adsobed fibrinogen, fibronectin, von Willebrand factor and vitronectin on the on the procoagulant state of adherent platelets, Biomaterials, 2000, 2243-2252, 21.
Helluin et al., The Activation State of avB3 Regulates Platelet and Lymphocyte Adhesion to Intact and Thrombin-cleaved Osteopontin, The Journal of Biological Chemistry, 2000, 976-983, 3.
Polanowska-Grabowska, et al., Platelet Adhesion to Collagen Type 1, Collagen Type IV, von Willebrand Factor, Fibronectin, Laminin, and Fibrinogen: Rapid Kinetics under Shear, Thrombosis and Haemostasis, 1999, 118-123, 81.
Sobel, et al., Herapin modulates integrin function in human platelets, Journal of Vascular Surgery, 2001, 587-594, 33.
Ovadia, et al., Transcatheter Uterine Artery Embolization for the Management of Symptomatic Uterine Leiomyomas, Obstetrical & Gynecological Survey, 1999, 745, 5, Lippincott Williams & Wilkins, Inc.
Iqbal, et al., Pulmonary arteriovenous malformations: a clinical review, Postgrad Medical Journal, 2000. 390-394, 76.
Sanchez, et al., Pseudoaneurysm of the Superficial Temporal Artery Treated by Embolization: Report of a Case, Journal of Oral Maxillofac Surgery, 2000, 819-821, 58.
Luchtefeld, et al., Evaluation of Transarterial Emoblization of Lower Gastrointestinal Bleeding, Dis Colon Rectum, 2000, 532-534, 43.
Eddy, Jean-Baptiste, Clinical assessment and management of massive hemoptysis, Critical Care Medicine, 2000, 1642-1647, 28, Lippincott Williams & Wilkins, Inc.

* cited by examiner

*Primary Examiner* — Michael Szperka
(74) *Attorney, Agent, or Firm* — William J. Bundren

(57) ABSTRACT

The present invention relates generally to methods and compositions for treating a disease or condition by administering a first therapeutic protocol comprising targeting and delivering solid-phase platelet-dependent vascular occlusion agents, and administering at least one second therapeutic composition or method.

15 Claims, No Drawings

METHODS OF TREATMENT USING VASCULAR OCCLUSION IN COMBINATION THERAPIES

CROSS-REFERENCE TO RELATED APPLICATIONS

This application is a continuation-in-part of U.S. application Ser. No. 10/241,717 filed Sep. 21, 2002 (now allowed), and U.S. application Ser. No. 10/101,731 filed Mar. 21, 2002, and the non-provisional of 60/708,757 filed Aug. 17, 2005.

FEDERAL SPONSORSHIP

Not Applicable

BACKGROUND OF THE INVENTION

The present invention is directed to methods for producing a therapeutic benefit by producing vascular occlusion using platelet activation as the initiating event in combination with one or more therapies. Compositions and methods of the invention involve delivering a solid-phase platelet-binding agent to a target site, causing platelets to bind and activate thereby forming a localized thrombus. Occlusion of the vasculature of the target tissue by the localized thrombus results in deprivation of essential oxygen and nutrients, in turn leading to tissue regression and ultimately tissue death.

DESCRIPTION OF RELATED ART

Platelets function in the body to limit blood loss in the event of vascular damage. Normally, platelets circulate throughout the body with other cellular components of blood, bathed in a mixture of various plasma proteins many of which play key roles in the clotting process. Upon exposure of vascular sub-endothelium: a complex series of events occurs to limit the loss of blood from the damaged vessel. Circulating platelets contacting components of the exposed sub-endothelium: 1) bind and adhere, 2) spread across the exposed surface, 3) activate as evidenced by release of granule contents, 4) aggregate and recruit other circulating platelets from the blood stream, and 5) form an efficient plug, clot, and/or thrombus stemming the flow of blood from the vessel.

One approach to overcoming the deficiencies of targeting tumors with antibodies would be to target thrombus-inducing agents to the vasculature of the tumor rather than to the tumor.

The present inventors propose that this approach will provide several advantages over targeting tumor cells directly. Firstly, the target cells are directly accessible to vascularly administered therapeutic agents permitting rapid localization of a high percentage of the injected dose. Secondly, since each capillary provides oxygen and nutrients for thousands of cells in its surrounding cord of tumor, even limited damage to the tumor vasculature could produce an avalanche of tumor cell death.

Under certain clinical situations, inhibition of blood flow to a tissue through occlusion of its associated vasculature is desirable. Examples include treatment of: hepatocellular carcinoma (HCC), renal cell carcinoma (RCC), hemorrhagic stroke, saphenous vein side branches in saphenous bypass graft surgery, aortic aneurysm vascular malformations, and solid tumors. Embolization of tumor vasculature prior to organ transplantation, and embolization of vasculature prior to tissue or organ resection is also desirable.

HCC ranks among the most common malignancies worldwide, and the prognosis for patients with HOC is typically poor. Hepatocellular tumors derive their blood supply nearly exclusively from the hepatic artery. As a result, an arterial approach to anti-tumor therapy is designed to spare the surrounding hepatic parenchyma, including selective tumor necrosis. There are many treatments currently being used and tested (e.g. chemoembolization, resection immunotherapy, and external radiation). Maintenance of arterial patency is important in some therapies.

Vascular occlusion has been performed using a variety of techniques and materials including embolotherapy. Examples of embolotherapy include the use of particles composed of a variety of materials including polyvinyl alcohol (Boschetti, PCT W00023054), acrylamide (Boschetti et al. U.S. Pat. No. 5,635,215; Boschetti et al, U.S. Pat. No. 5,648, 100), polymethyl methacrylate (Lemperie, U.S. Pat. No. 5,344,452), physical plugs composed of collagen (Conston et al, U.S. Pat. No. 5,456,693) and coils (Mariant, U.S. Pat. No. 5,639,277). Embolotherapy involves the delivery of these materials to the target vasculature by means of a catheter. Since the vasculature in most locations proceeds from larger arteries to arterioles to metarterioles to capillaries, each with progressively smaller vessel diameters, the delivered material (embolus) continues to travel in the flowing blood until it becomes lodged in the smaller blood vessels thereby impeding the flow of blood to the dependent tissue.

Unfortunately, the suspension mediums currently used cause only temporary or semi-permanent vascular occlusion. A number of the treatments, such as transcatheter arterial chemoembolization, which involves localized intra-arterial infusion of chemotherapy, emulsified oil, and an embolic material, provide better tumor response when repeated multiple times, so long-term arterial patency may be critical to the success of chemoembolization.

Other therapies have moderate success, but only resection or transplantation is seen as curative treatments. For example, interferon has been reported to reduce the risk of HCC, but there is conflicting evidence in patients who have already developed cirrhosis. Further, the possibility that interferon has anticarcinogenic effects unrelated to its antiviral efficacy is now widely accepted, but remains unproven. Internal radiation, e.g. 131-I-Lipiodol is used as a vehicle for chemotherapy, but does not achieve arterial occlusion. Percutaneous Ethanol Injection (PEI) is widely used to treat HCC. However, during the follow-up period after PEI, local recurrence was seen in approximately 10% of PEI-treated nodules.

Radiofrequency (RF) ablation is the most extensively used alternative to PEI. RF can be applied percutaneously, laparoscopically, or during laparotomy. Yet, robust survival advantages have not been proven.

As a result there is still a need for a method to enhance the effectiveness and success rates of current treatments. The present invention seeks to address this need by combining two or more therapies either, serially or in parallel to achieve a therapeutic benefit.

The present invention is novel and addresses unmet medical needs through the use of a solid-phase material, such as microparticles or coils or stents, configured or adapted to activate platelets. In some embodiments of the invention, the solid-phase material itself binds and activates platelets, in other embodiments, the solid-phase material may be coated with von Willebrand factor (VWF) of mammalian origin. In this way a therapeutic benefit may be achieved by delivering a solid-phase platelet binding agent to a target site and initiating efficient thrombus formation leading to occlusion of the associated vasculature in combination with one or more therapies.

SUMMARY OF THE INVENTION

The present invention relates to therapeutic methods and compositions for targeting tissues and/or organs, and associated vasculature, which are hyperplastic or neoplastic in nature, or which have arterio-venous malformations, or which are hemorrhaging, using solid-phase agents that induce thrombus formation via localized platelet activation.

The present invention relates to therapeutic methods for producing vascular occlusion using a solid-phase agent in combination with one or more therapies, said therapy comprising any medical, pharmaceutical, or biological therapy or agent. Exemplary therapies or agents include, but are not limited to chemotherapy, chemoembolization, radiofrequency ablation, microwave treatment, cryoablation, percutaneous ethanol injection, resection, transplantation, angiogenesis inhibitors, immunotherapy, tyrosine kinase inhibitors, interferon, internal radiation, external radiation, cytostatic agents, gene therapy, embolic agents, hormone therapies, and growth factor receptor inhibitors. As used herein, in combination refers to administering two separate therapies whereby the overall health of the patient is improved. The therapies may be administered either serially or in parallel.

The composition comprises a solid phase agent for capturing platelets on a solid-phase agent such as a coil or a stent or a particle. In some embodiments of the invention, the solid-phase agent both captures and activates the platelets. The method utilizes localizing platelet collection and activating the platelets on the solid-phase particle to produce subsequent thrombus formation, thereby limiting the blood supply to the target area, without inducing a generalized or systemic pro-thrombotic state.

Contact of the solid-phase platelet-binding agent with the blood from a patient (ex vivo) or in the blood stream (in vivo) induces platelet binding and localized activation leading to accretion of platelets about the solid-phase agent leading to thrombosis and cessation of blood flow to the tissue supplied by the occluded blood vessel(s). Cells, including tumor cells or hyperplastic tissue, diminish or die as a result of loss of localized blood flow. This approach avoids systemic platelet activation and thrombosis. For example, immobilized VWF (but not soluble VWF) binds to and activates circulating platelets. Thus, the methods and compositions of the present invention comprise both an indirect and direct means of treating any pathological condition where blood is involved or present, such as cancer, hyperplastic cells, excessive bleeding or arteriovenous (AV) malformations.

The present invention improves on existing methods for treating solid hyperplastic tissue, excessive bleeding and AV-malformations and any other tumors, hyperplastic disease or condition in which platelets (resting and/or activated) may play a therapeutic role.

In a manner similar to an existing pathological condition (ie. Heparin-Induced Thrombocytopenia [HIT]), localized platelet activation can be enhanced by means of an Fc-mediated process by including or incorporating a human Fc fragment onto the solid-phase agent, or by directing select antibodies to the target area. Platelet activation in HIT syndrome results in localized thrombosis and cessation of blood flow to the affected area. This leads to death of the affected tissue.

The extent or degree of site-specific thrombosis can be controlled in a variety of ways. Inhibition of platelet activation through the use of anti-platelet agents (eg. GPIIb/IIIa inhibitors, aspirin, dipyridamole, etc.) decreases the propensity to induce a thrombus in a defined, titratable manner. Altering local blood flow, blood pressure and tissue temperature can also serve as means of controlling local platelet activation to a stimulus.

Typical vascularized tumors are the solid tumors, particularly carcinomas, which require a rich vascular blood supply. Exemplary solid tumors to which the present invention is directed include, but are not limited to, primary malignant tumors of the lung, breast, ovary, stomach, pancreas, larynx, esophagus, testes, liver, parotid, biliary tract, colon, rectum, cervix, uterus, endometrium, kidney, bladder, prostate, thyroid, head and neck, melanomas, gliomas, neuroblastomas, neuroendocrine tumors, and the like. Other conditions to which the present invention is directed include, but are not limited to, secondary (metastatic) tumors of the above mentioned tumor types, cancer pain, AV-malformations, uterine fibroids, pelvic congestion, menorrhagia, varicoceles, hemoptysis, aneurysms, visceral artery aneurysms, pseudoaneurysms and endoleaks.

A preferred method of the invention includes preparing a coil or stent coated with VWF of recombinant or mammalian origin and introducing the VWF-coated agent into the bloodstream of an animal, such as a human patient, an animal patient, or a test animal; the VWF is then delivered or collects at a desired target site. The coils or stents can be constructed of any suitable material capable of retaining VWF either within the coil or stent or on the surface of the coil or stent for an indefinite or varying length of time.

A solution to the problem of the unrestrained growth of solid tumors is to attack the blood vessels in the tumor. This approach offers several advantages over methods that directly target tumor cells. Firstly, the tumor vessels are directly accessible to vascularly administered therapeutic agents, thus permitting rapid localization of high percentage of the injected dose. Secondly, since each capillary provides oxygen and nutrients for thousands of cells in its surrounding cord of tumor even limited damage to the tumor vasculature could produce extensive tumor cell death. Finally, blood vessels are similar in different tumors, making it feasible to develop a single reagent for treating numerous types of cancer.

DESCRIPTION OF THE DRAWINGS

Not Applicable

DETAILED DESCRIPTION OF THE INVENTION

The present invention provides compositions and methods for capturing platelets at a predetermined site, activating the platelets, and harnessing the natural function of platelets to achieve a beneficial therapeutic result. In accordance with the present invention, the platelets may be circulating platelets or may be platelets obtained from an external source. In accordance with the present invention, platelets may be targeted to a specific site, and then the natural ability of platelets to induce thrombus formation may be used to interrupt, disrupt, or reduce blood flow at the site. Reduced blood flow concomitantly reduces nutrient supply to a disease or condition agent, such as a tumor, so the size of the disease agent is diminished. It is clear that reducing the size of a tumor is an obvious therapeutic benefit. In some instances reduction of the blood supply to a target area alleviates pain.

The present invention relates to therapeutic methods for producing vascular occlusion using a solid-phase agent in combination with one or more therapies, as used herein combined refers to using one or more additional protocols together in any manner that results in a therapeutically beneficial result or outcome for the patient. For example, two or more therapies may be combined serially or in conjunction with one another. It is intended that two or more therapies should be combined if it is determined that the patient's health will benefit, or that it is believed that the patients health will benefit.

The present invention also includes targeting platelets to a pre-determined tissue capable of being selectively targeted, e g., hyperplastic tissue, using a solid-phase agent capable of binding and activating the platelets. In these embodiments of the invention, targeting refers to the solid phase containing a targeting moiety, e.g., a ligand or the like, that specifically binds the pre-determined site or tissue. In other embodiments of the invention, targeting may include delivering a composition of the present invention at or near a tumor site. e.g., by catheter, stent, or coil. Activating the platelets at the pre-selected site causes a therapeutic benefit by reducing the nutrient supply to the tissue or site. U.S. Pat. Nos. 6,960,532; 6,887,474; and U.S. Ser. No. 11/205,047 (filed Aug. 17, 2005), each incorporated herein by reference The present invention provides compositions and methods for inducing thrombus formation by capturing platelets on the solid-phase agent, inducing activation of the platelets, and allowing a thrombus to form. Thrombus formation in the target vasculature reduces the blood supply to the downstream tissue. By capturing platelets on a VWF-containing, or collagen-containing solid phase (e.g., coated particles), the compositions and methods of the present invention may be used to treat cancer, hyperplasia, uterine fibroids, pelvic congestion, menorrhagia, AV-malformations, neuro-embolism, varicoceles, hemoptysis, visceral artery aneurysms, arterial aneurysms, endoleaks, and the like. Furthermore, the compositions and methods of the present invention provide a therapeutic benefit to the recipient of the composition.

In a preferred embodiment of the invention, the VWF is of mammalian origin. In a most preferred embodiment of the invention, the VWF is of human origin. In a further most preferred embodiment of the invention, the VWF is of porcine origin.

The VWF may be natural, synthetic, recombinant, or a peptide sequence conforming to a biologically active portion of VAFd In a further most preferred embodiment of the invention the VWF is of recombinant origin.

In a preferred embodiment of the invention, the collagen is of mammalian origin. In a most preferred embodiment of the invention, the collagen is of human origin. In a further most preferred embodiment of the invention, the collagen is of bovine origin or porcine origin. In a further most preferred embodiment of the invention, the collagen is of recombinant origin.

The present invention also provides compositions that bind a platelet-binding agent (e.g. VWF or collagen) directly or indirectly through a spacer to the solid phase, so long as the ability of the platelet-binding agent to bind platelets is not impaired. Spacer, as used herein, refers to a group of inert or active molecules that physically separate the platelet binding agent from the surface of the solid phase agent. Exemplary spacers are described below. The direct binding can occur either covalently or non-covalently. Indirect binding can occur through spacers, including but not limited to peptide spacer arms, spacers, antibody fragment spacers, fusion protein spacers or antibody carbohydrate spacers. These spacers normally act only as bridges between the particle and the platelet binding agent; however, the spacers could also be used to alter the degree of platelet activation. For example, an Fc component could be used as a spacer, thereby effecting enhanced platelet activation on and about the solid-phase agent. Coupling of platelet binding agent (e.g. VWF or collagen) to the solid phase agent can occur using methods known to those skilled in the art. Examples of coupling agents include but are not limited to glutaraldehyde, succinimide esters, benzidine, periodate and carbodiimide.

In a preferred embodiment of the invention, the positioning within the vascular system of mammals of compositions without an active targeting agent would be selected by blood flow directed positioning following delivery by means of a superselective microcatheter.

Compositions according to the present invention may also include a targeting agent or moiety capable of binding a target antigen or site on the vascular endothelium or target tissue thereby enabling localization of the solid-phase agent to a selected site. Exemplary targeting agents or moieties are well known to those skilled in the art, and include, but are not limited to antibodies, ligands, receptors, hormones, lectins, and cadherins, or portions or fragments thereof. U.S. Pat. Nos. 6,960,532; 6,887,474; and U.S. Ser. No. 11/205,047 (filed Aug. 17, 2005), each incorporated herein by reference In a preferred embodiment of the invention, the targeting agent would include an antibody or antibody-like molecule with biotin, biotin mimetic and/or a peptide component. In a further preferred embodiment of the invention, the antibody or antibody-like molecules would be directed toward a growth factor/receptor complex.

Compositions according to the invention may also include one or more of the following: one or more platelet binding modulators (e.g., inhibitors or enhancers), one or more thrombus formation controllers or modulators or one or more complement cascade components.

Methods according to the invention may also include administering a solid-phase agent capable of binding platelets at a pre-determined site; may also include inducing activation of the captured platelets, administering a bifunctional binding agent having an antigenic determinant and a platelet binding site; controlling thrombus generation by altering the temperature of one or more compositions of the invention, or by altering the temperature at the pre-selected site.

Methods according to the invention may further include one or more of the following: administering one or more platelet binding modulators, administering one or more thrombus formation modulators-; administering one or more complement cascade components, administering one or more ligands and/or anti-ligands for binding the solid phase to a pre-determined site, and/or for binding a platelet binding moiety or component to the solid phase.

The present invention also includes a kit which may contain but is not limited to any or all of the following components including a solid-phase agent for targeting platelets to an endothelial membrane component: a binding agent for binding platelets; a ligand for binding an endothelial membrane component, a ligand conjugate; an anti-ligand for binding the ligand or the ligand conjugate; a platelet binding modulator (enhancer and/or inhibitor); a thrombus formation modulator; a complement cascade component; a complement cascade component inducer; and a binding agent for binding platelets that includes an anti-ligand. The kit may include a bifunctional binding agent, and/or a binding agent-ligand conjugate, and/or a platelet-binding agent -anti-ligand conjugate.

The compositions and methods of the present invention include any mechanism of delivering a composition to the pre-selected site, including but not limited to systemically, locally, orally, or topically.

In accordance with some embodiments of the invention, binding agents are used to capture platelets at a predetermined site.

Definitions:

As used herein, a solid-phase agent refers to any solid material suitable for binding, containing, or retaining a platelet-binding agent. The platelet-binding agent may be attached to the solid-phase agent such that platelet binding activity is retained, e.g. at or within a target site. The solid phase agent may be a coil, stent, or particle, e.g., a bead or the like all of which are well known to those skilled in the art U.S. Pat. Nos. 6,960,532; 6,887,474; and U.S. Ser. No. 11/205,047 (filed Aug. 17, 2005) each incorporated herein by reference As used herein, a particle refers to a discrete portion or part of a solid-phase material capable of containing or retaining a platelet-binding agent. A preferred method of the invention includes preparing a particle coated with VWF of recombinant or mammalian origin and introducing the VWF-coated particle into the bloodstream of an animal, such as a human patient, an animal patient, or a test animal.

A preferred method of the invention includes preparing a particle coated with coliagen of recombinant or mammalian origin and introducing the coliagen-coated particle into the bloodstream of an animal, such as a human patient, an animal patient, or a test animal.

As used herein, the term "particle" refers to any solid-phase material capable of binding platelets, either directly or indirectly (e.g. through ligands). The particles can be homogenous or heterogeneous as related to size. Specifically, the particles can be of spherical (including ovoid) or irregular shape. The particles can be constructed of any suitable material capable of retaining VWF or collagen either within the particle or on the surface of the particle for an indefinite or varying lengths of time. Exemplary materials include polyvinyl alcohol (PVA), polystyrene, polycarbonate, polylactide, polyglycolide, lactide glycolide copolymers, polycaprolactone, lactide-caprolactone copolymers, polyhydroxybutyrate, polyalkylcyanoacrylates, polyanhydrides, polyorthoesters, albumin, collagen, gelatin, polysaccharides, dextrans, starches, methyl methacrylate, methacrylic acid, hydroxylalkyl acrylates, hydroxylalkyl methacrylates, methylene glycol dimethacrylate, acrylamide, bisacrylamide, cellulose-based polymers, ethylene glycol polymers and copolymers, oxyethylene and oxypropylene polymers, polyvinyl acetate, polyvinylpyrrolidone and polyvinylpyridine, magnetic particles, fluorescent particles, animal cells, plant cells, macro-aggregated and micro-aggregated albumin, denatured protein aggregates and liposomes, used singly or in combination. The solid phase materials suitable for use in the present invention are well known to those skilled in the art, and should not be limited to those exemplary materials recited above.

Exemplary materials for forming the stent or coil include, but are not limited to: polyvinyl alcohol (PVA), polystyrene, polycarbonate, polylactide, polyglycolide, lactide-glycolide copolymers, polycaprolactone, lactide-caprolactone copolymers, polyhydroxybutyrate, polyalkylcyanoacrylates, polyanhydrides, polyorthoesters, polysaccharides, dextrans, starches, methyl methacrylate, methacrylic acid, hydroxyalkyl acrylates, hydroxyalkyl methacrylates, methylene glycol dimethacrylate, acrylamide, bisacrylamide, cellulose-based polymers, ethylene glycol polymers and copolymers, oxyethylene and oxypropylene polymers, polyvinyl acetate, polyvinyl pyrrolidone and polyvinylpyridine; magnetic materials, fluorescent materials gold, platinum, palladium, rhenium, rhodium, ruthenium, stainless steel, tungsten, titanium, nickel and alloys thereof used singly or in combination.

The preferred size of the solid phase material depends on the type of material being used. For example, those skilled in the art wilt recognize that if the solid phase is a stent or coil, the size is preferably of a diameter that fits within a blood vessel, such as an artery. Typically the diameter will be up to about 15 mm or greater. If the solid phase is a particle, such as a bead, the diameter may be up to about 7 mm, preferably from about 1 µm to about 5 mm, even more preferably from about 20 µm to about 300 µm. The size of solid phase materials suitable for use in the present invention are well known to those skilled in the art, and should not be limited to the exemplary sizes recited above.

As used herein, a binding agent or targeting moiety refers to one or more solid phase chemical or biological molecules or structures for binding one substance to another. Specifically the binding agent, or solid phase agent, binds a ligand, a receptor or a ligand/receptor complex on a defined population of cells, typically hyperplastic tissue and/or associated vasculature, or a cancer cell and/or associated vasculature. A molecule's function as a binding agent should not be limited by the structural mechanism of attachment. For example, a binding agent may bind a receptor, an antigenic determinant or epitope, an enzymatic substrate, or other biological structure agent to a target cell or cell population. The binding agent may be a conjugate, and includes but is not limited to immunological conjugates, chemical conjugates (covalent or non-covalent), fusion proteins, and the like. U.S. Pat. Nos. 6,960, 532; 6,887,474; and U.S. Ser. No. 11/205,047 (filed Aug. 17, 2005), each incorporated herein by reference As used herein, a ligand-binding agent refers to a complementary set of molecules that demonstrate specific binding for each other. A ligand/anti-ligand pair generally binds with relatively high affinity, and for this reason, may be highly desirable for use with the present invention. A very well known ligand/anti-ligand pair is biotin and avidin. As used herein, avidin refers to avidin, streptavidin, neutravidin, derivatives and analogs thereof, and functional equivalents thereof. Avidin may bind biotin in a multivalent or univalent manner. Other exemplary ligand/anti-ligand pairs include, but are not limited to homophyllic peptides, heterophyllic peptides, "leucine zippers" zinc finger proteins/ds DNA fragment, enzyme/enzyme inhibitor, hapten/antibody, ligand/ ligand receptor, and growth factor/growth factor receptor.

As used herein, a selected site, a pre-determined site, targeting, and pre-targeting all refer to a site where the accumulation of platelets about a solid-phase will provide a therapeutically beneficial result. Typically, this involves target site localization of a targeting moiety. Such sites include, but are not limited to, the vasculature of solid tumors, the vasculature of benign tumors, the vasculature of hyperplastic tissue(s), the vasculature of hyper-vascularized tissues, AV-malformations, vessel aneurysms and endoleaks. U.S. Pat. Nos. 6,960, 532; 6,887,474; and U.S. Ser. No. 11/205,047 (filed Aug. 17, 2005), each incorporated herein by reference As used herein, delivery of the solid agent comprising a platelet-binding agent can occur using a catheter, a microcatheter or by needle and syringe. Delivery by a microcatheter is most often achieved by access through the arterial circuit, however delivery of the solid agent through the venous circuit is also desirable. As an example, the solid agent in the form of particles, coils or stents can be delivered by catheter, to target site using the arterial or venous circuits. Delivery of the solid agent using arterial circuit is advantageous since the capillary beds downstream of applied agent in the target tissue act as a means of trapping the agent, thereby preventing the agent from entering the systemic circulation. The solid agent can also be localized within the arterial circulation using a targeting agent associated with the solid agent. Delivery of the solid agent using the venous system is also desirable. Localized delivery of the solid agent in the venous system can be accomplished by binding the solid agent to the target site using a targeting agent associated with the solid agent. The solid agent can also be delivered to the target site during a surgical procedure. As an example, the solid agent in the form of particles can be delivered by syringe and needle to the target site. As a further example, the solid agent in the form of a coil or stent can be placed manually at the target site during the surgical procedure.

As used herein, thrombus refers to any semi-solid aggregate of blood cells enmeshed in fibril and clumps of platelets originating from platelets actively binding to the solid-phase agent. In accordance with the invention, a thrombus is formed as a direct result of activated platelet accumulation at the pre-determined site. Thrombosis refers to the formation of a thrombus, typically within a blood vessel. Thrombotic refers to substances that tend to cause thrombosis, or are thrombus forming.

As used herein, embolus refers to an intravascular mass, which travels through the bloodstream, and through size constraints eventually becomes lodged in a blood vessel or capillary, distal from the site of origin of the intravascular mass. Embolization does not imply an active process, but instead refers to a passive process whereby occlusion of blood vessels occurs by intravascular masses traveling through the blood stream where they become lodged in Somali blood vessels and capillaries.

In contrast, the present invention involves the delivery of solid-phase material to target vasculature whereupon platelets are actively recruited to the solid-phase surface through the use of a platelet-binding agent. In contrast to embroiling materials described in cited patents, included herein as reference, the agents of the present invention must be delivered in close proximity to the target vasculature due to rapid accumulation of platelets about the solid-phase material.

By way of example, macro-aggregated albumin (MAA), as supplied by Drainage (Kirkland, Quebec Canada), for example, is used as an embroiling imaging agent. The MAA consists of particles between 10 μm and 70 μm in size, with a maximum size of 150 μm that are radiolabeled with sodium pertechnetate Tc 99 m to enable scintigraphy imaging. The MAA particles are injected intravenously, and travel through the blood stream as emboli where they become trapped in the pulmonary alveolar capillary bed. Using the method of the present invention, immobilization of VWF on the MAA, with subsequent injection of the particles into the vascular system, most preferably upstream Of the target tissue, causes immediate platelet binding to the particles and occlusion of the vasculature in close proximity to the site of injection.

As used herein, combination therapy or similar phrases, refers to administering a solid phase embodiment of the present invention in combination with any other therapy. The purpose of such combination treatment is to derive a beneficial affect for the patient.

The present invention improves upon existing methods of producing vascular occlusion by securing platelets to the surface of a solid-phase material through the use of a platelet-binding agent, thereby increasing the effective size of the solid-phase material. For example, a particle coated with or containing VWF, which is injected into the blood stream, would rapidly accumulate platelets on its surface, in effect producing an 'onion-effect' of layered, activated platelets in close proximity to the injection site. Therefore the present invention enables delivery of a minimum number of small particles into the bloodstream, whereupon the particles rapidly grow in size from the accretion of platelets actively binding to the platelet-binding agent on or within the particle. Furthermore, the particle-bound platelets would interact with each other thereby forming aggregates of increasing size producing a tight matrix and effecting occlusion of the target vasculature.

The present invention further improves upon existing methods of producing vascular occlusion by securing platelets to the surface of a solid-phase material by means of a platelet-binding agent. The agent of the invention would therefore have the following effects in vivo: a) molding to the contours of the blood vessel or capillary in which it resides, b) producing a solid, impermeable three-dimensional matrix; this in turn produces a tight, impermeable seal within the vessel, thereby maximally inhibiting the delivery of blood to downstream blood vessels and tissues.

For example, the introduction of a platelet-binding particle into the blood stream would proceed through the following sequence of events, a) a single layer of platelets would form on the surface of the particle thereby forming (i) a particle of increased diameter and (ii) a particle coated with activated platelets with the propensity to bind and activate nearby platelets in suspension, herein defined as 'single-layered surface activated platelets' particle (S-SAP particle), b) platelets flowing in the blood stream would interact with platelets bound to the S-SAP particle forming 'onion-like' layers herein defined as multi-layered surface activated platelet particle (M-SAP particle), c) M-SAP would interact with each other through platelet/platelet interaction forming larger aggregates, herein defined as the 'M-SAP matrix'.

As a further example, the introduction of an amorphous platelet binding particle (e.g., MAA) containing or having a surface-bound platelet-binding agent (e.g., VWF) into the brood stream would proceed through the following sequence of events: a) single platelets would bind on and within the matrix of the particle thereby forming (i) a particle with increased diameter and rigidity, (ii) a particle coated with and containing activated platelets with the propensity to bind and activate nearby platelets in suspension: b) platelets flowing in the blood stream would interact with the platelets bound to and/or bound within the particle thereby forming aggregates within and/or on the particle, c) particles containing and/or having surface bound platelets would interact with each other to form large particle aggregates.

As used herein therapeutically beneficial, providing a therapeutic benefit or the like refers to a desirable change in the physiology of the recipient animal. In a preferred embodiment of the invention, the change is detectable. In accordance with the invention, any biological mechanism that involves activated platelets or platelet modulation may be used or harnessed to achieve a beneficial therapeutic result. Exemplary therapeutic benefits produced in accordance with the present invention include, but are not limited to, forming a thrombus, forming a platelet-mediated occlusion, eliminating a hyperplastic tissue or cells, eliminating a tumor and/or tumor cells, diminishing the size of a hyperplastic tissue, diminishing the size of a tumor, causing the hyperplastic tissue or tumor to become susceptible to additional therapies such as chemotherapy and/or radiation therapy or the like, starving or reducing the nutrient supply to a hyperplastic tissue or cancer, repairing AV-malformations, reducing or preventing blood loss from endoleaks and repairing vessel aneurysms.

Another exemplary therapeutic benefits produced in accordance with the present invention include, but are not limited to, forming a thrombus, forming a platelet mediated occlusion, eliminating a hyperplastic tissue or cells, eliminating a tumor and/or tumor cells, diminishing the size of a hyperplastic tissue, diminishing the size of a tumor, in combination with additional therapies either serially or alongside such as surgery, chemotherapy, chemobembolization, local ablation treatments, immunotherapy, angiogenesis inhibition and/or radiation.

As used herein, "administering." refers to any action that results in contacting or delivering a composition containing a solid-phase agent to a pre-determined cell, cells, or tissue, typically mammalian. Administering may be conducted in vivo, in vitro, or ex vivo. For example, a composition may be administered by injection or through an endoscope or catheter. Administering also includes the direct application to cells of a composition according to the present invention. For example, during the course of surgery, the vasculature of tumor or hyperplastic tissue may be exposed. In accordance with an embodiment of the invention, the exposed cells or vasculature may be exposed directly to a composition of the present invention, e g., by washing or irrigating the surgical site, vasculature, and/or the cells.

The solid-phase platelet-binding agent can be localized to a specific target site using a binding or targeting agent. Exemplary binding or targeting agents include, but are not limited to: monoclonal antibodies; polyclonal antibodies; chimeric monoclonal antibodies; humanized antibodies; genetically engineered antibodies; fragments of antibodies, selected from the group consisting of F(ab)2, F(ab')2, Fab, F(ab'), Dab, Fv, sFv, scFv, Fcy and minimal recognition unit; single chains representing the reactive portion of monoclonal antibodies (SC-MAb); tumor-binding peptides; a protein, including receptor proteins; peptide; polypeptide; glycoprotein; lipoprotein, or the like, e.g., growth factors; lymphokines and cytokines; enzymes, immune modulators; hormones, for example, somatostatin; a ligand (paired with its complementary anti-ligand); oligonucleotides; any of the above joined to a molecule that mediates an-effector function; and mimics or fragments of any of the above. Analogs of the above-listed targeting moieties that retain the capacity to bind to a defined target cell population may also be used within the claimed invention. In addition, synthetic targeting moieties may be designed.

Monoclonal antibodies useful in the practice of the present invention include whole antibodies and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins, which employ sequences from more than one species. See, generally, Kohler and Milstein, Nature, 256:495-97, 1975; Eur. J. Immunol., 6:511-19, 1976. The preferred binding and/or targeting agent capable of localizing the solid-phase agent to a target site is an antibody or antibody-like molecule, preferably a monoclonal antibody. A more preferred binding agent is an antibody that binds a ligand/receptor complex on hyperplastic tissue or cells (e.g., tumor) or the vasculature associated with hyperplastic tissue or cells. The most preferred binding agent is an antibody or antibody-like molecule that binds a growth factor/growth factor receptor complex either on or in the vicinity of the tumor mass such as the tumor vasculature. In a preferred embodiment of the invention, the binding agent (i.e.: antibody or antibody-like molecules) would bind to the VEGFNEGF receptor complex. In a further preferred embodiment of the invention, the antibody or antibody-like molecule binding would recognize a neo-epitope (cryptic or previously unavailable epitope) formed due to ligand/receptor (i,e., growth factor/growth factor receptor) interaction. In a further preferred embodiment of the invention, the binding of the antibody or antibody-like molecules to the growth factor/growth factor receptor complex would not affect the function of either the growth factor or the growth factor receptor.

As used herein, VEGF receptor refers to all members of the Vascular Endothelial Growth Factor Receptor family, including but not limited to FLT1/VEGFR, FLK1/KDR/VEGFR2, and FLT4/VEGFR3.

As used herein "causing a tissue or tumor to become susceptible to additional therapies" refers to inducing a condition of low nutrient and/or oxygen supply to the tissue or tumor, through the method of the present invention including, but not limited to, forming a thrombus in the tumor vasculature and/or causing a reduced blood supply to the tumor.

Exemplary proteins useful in the practice of this invention include but are not limited to proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor). Oligonucleotides, e.g.; anti-sense oligonucleotides that are complementary to portions of target cell nucleic acids (DNA or RNA), are also useful as targeting moieties in the practice of the present invention. Oligonucleotides binding to cell surfaces are also useful.

Any growth factor may be used for such a targeting purpose so long as it binds to a tumor or tumor-associated endothelial cell. Suitable growth factors for targeting include but are not limited to VEGF/VPF (vascular endothelial growth factor/vascular permeability factor), FGF (which, as used herein refers to the fibroblast growth factor family of proteins), TGFb (transforming growth factor b), EGF and pleitotropin. Preferably the growth factor receptor to which the targeting factor binds should be present at a higher concentration on the surface of tumor-associated endothelial cells than on non-tumor associated endothelial cells. Most preferably, the growth factor receptor to which the targeting growth factor binds should further be present at a higher concentration on the surface of tumor-associated endothelial cell than on any non-tumor-associated cell type.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity such minimal polypeptides exhibiting the binding affinity of the targeting moiety.

The Fv fragments of immunoglobulins have many significant advantages over whole immunoglobulins for the purpose of targeted tumor therapy, including better lesion penetration on solid tumor tissue and more rapid blood clearance, as well as potentially lower Fc-mediated immunogenicity. An exemplary single-chain Fv (scFv) binding agent may be engineered from the genes isolated from the variable regions of antibodies recognizing a ligand/receptor complex.

An embodiment of the invention involves a targeting agent having a binding affinity for a marker found, expressed, accessible to binding, or otherwise localized on the cell surfaces of tumor-associated vascular endothelial cells as compared to normal non-tumor-associated vasculature. Further, certain markers for which a targeting agent has a binding affinity may be associated with components of the tumor-associated vasculature rather than on the tumor-associated endothelial cells, themselves. For example, such markers may be located on basement membranes or tumor-associated connective tissue.

It may be desirable to prepare and employ an antibody or other binding agent or moiety having a relatively high degree of selectivity for tumor vasculature, together with little or no reactivity with the cell surface of normal endothelial cells as assessed by immunostaining of tissue sections. It may also be desirable to prepare and employ an antibody or other binding agent or moiety capable of binding an epitope common to all vasculature.

Any composition that includes a solid-phase platelet-binding agent with or without a targeting agent according to the invention may be used to initiate an in vivo therapeutic benefit, thrombus formation, and/or cell killing or regression. The composition may include one or more adjuvants, one or more carriers, one or more excipients, one or more stabilizers, one or more permeating agents (e.g., agents that modulated movement across a cell membrane), one or more imaging reagents, one or more effectors, and/or physiologically-acceptable saline and buffers. Generally, adjuvants are substances mixed with an immunogen in order to elicit a more marked immune response. The composition may also include pharmaceutically acceptable carriers. Pharmaceutically acceptable carriers include, but are not limited to, saline, sterile water, phosphate buffered saline, and the like. Other buffering agents, dispersing agents, and inert non-toxic substances suitable for delivery to a patient may be included in the compositions of the present invention. The compositions may be solutions suitable for administration, and are typically sterile, non-pyrogenic and free of undesirable particulate matter. The compositions may be sterilized by conventional sterilization techniques.

In a preferred embodiment of the invention, a suitable composition includes a binding or targeting agent that binds to ligand/receptor complex. Exemplary antigens useful as targets in accordance with the present invention include, but are not limited to, antigens associated with cancer, including, lung, colon, rectum, breast, ovary, prostate gland, head, neck, bone, immune system, blood, or any other anatomical location. Exemplary antigens and/or pre-determined sites include but are not limited to VEGF/VEGF receptor complex, FGF/FGF receptor complex, or TGF beta/TGF beta receptor complex, p-selectin, sialyil-lewis X, endothelin, endothelin receptor, endothelin/endothelin receptor complex, alpha-fetoprotein, platelet-endothelial cell adhesion molecule (PECAM), CD31, CD34, CD36, glycoprotein Ib (GPIb), endoglin, thrombomodulin, endothelial leukocyte adhesion molecule (ELAM), intercellular adhesion molecule 1 (ICAM-1), MHC-I, and MHC-II. The subject may be a human or animal subject.

As noted above, a composition or method of the present invention includes a platelet binding agent or component. Exemplary platelet binding agents or components include but are not limited to von Willebrand factor (VWF), osteopontin, fibrinogen, fibrin, fibronectin, vitronectin, collagen, thrombospondin, laminin, heparin, heparan sulfate, chondroitin sulfate, phospholipase A2 (PLA2), matrix metal lop proteinases (MMPs), thrombin, glass, sialyl-lewis X, fibulin-1, platelet-endothelial cell adhesion molecule (PECAM), intercellular adhesion molecule 1 (ICAM-1), intercellular adhesion molecule 2 (ICAM-2), CD11 b/CD18 (MAC-1), CD11a/CD18 (LFA-1), p-selectin glycoprotein ligand 1 (PSGL-1), either singly or in combination.

As noted above, a composition or method of the present invention may include a platelet-mediated occlusion enhancer. The platelet-mediated occlusion enhancer may be a moiety that forms a portion of a bifunctional molecule as noted above, may be an ingredient in a composition according to the invention, and/or may be administered separately from a composition according to the invention.

Those skilled in the art will recognize that it may be desirable to include or use an occlusion enhancer when the individual receiving the therapy is in a state of compromised haemostasis. Under such conditions, the individual receiving the therapy has a propensity to bleed due to a pathological process that may have been acquired or is congenital in nature. Since the utility of the present invention is reliant upon the formation of a thrombus in the tissue or tumor vasculature after targeting platelets to the area, use of methods that augment platelet activation and/or the coagulation process could compensate for the individuals hemorrhagic tendencies. Examples of such conditions include, but are not limited to, haemophilia, von Willebrand's disease, coagulation factor deficiencies, Glanzmann's thrombasthenia, and Bernard Soulier Syndrome.

Exemplary platelet-mediated occlusion enhancers include but are not limited to ristocetin, thrombin, heparin-induced thrombocytopenia (HIT) antibodies or portions thereof, antiphospholipid antibodies (APA) or portions thereof, whole antibody molecules via an Fc-mediated mechanism, anti-LIES antibodies, anti-CD9 antibodies, epinephrine, thrombin receptor activating peptide (TRAP), proteinase-activated receptor (also known as protease activated receptor, PAR) agonists, cathepsin G, elastase, arachidonate, platelet activating factor (PAF), thromboxane A2 (TxA2), TxA2 mimetics, phospholipase A2 (PLA2), activators of protein kinase C (PKC), adenosine diphosphate (ADP), inducers of cyclo-oxygenase 1 (COX-1), inducers of cyclo-oxygenase 2 (COX-2): collagen, von Willebrand factor (VWF), matrix metalloproteinases (MMPs), heparin, heparan sulfate, chondroitin sulfate, ionophores, complement cascade components (e.g., C5b-9) platelet microparticles, platelet membrane fractions.

As noted above, a composition or method of the present invention may include a platelet-mediated occlusion retarder or the like. The platelet-mediated occlusion retarder may be a moiety that forms a portion of a bi-functional molecule as noted above, may be an ingredient in a composition according to the invention, and/or may be administered separately from a composition according to the invention. Those skilled in the art will recognize that it may be desirable to include or use a platelet-mediated occlusion retarder when the individual receiving therapy based on the method of the present invention has an underlying propensity to thrombose (i.e. form clots too rapidly and/or in inappropriate locations in the body). Although the method of the present invention is directed to the formation of a thrombus in the tumor vasculature, individuals with a propensity to thrombose may form thrombi in inappropriate locations during the course of the therapy described by the present invention. Use of agents to reduce the rapidity and/or extent of thrombosis could be used to minimize the risk of forming thrombi in inappropriate locations in the body. Examples of conditions whereby the individual receiving therapy encompassed by the present invention may require the use of occlusion retarders are, but are not limited to, coronary artery disease, acute myocardial infarction, transient ischemic attack, stroke, high blood pressure, ATIII deficiency, Protein C deficiency, Protein S deficiency, heparin-induced thrombocytopenia, deep vein thrombosis, peripheral vascular disease and/or Factor V Leiden deficiency.

Exemplary platelet-mediated occlusion retarders include but are not limited to aspirin, ibuprofen, acetaminophen, ketoprofen, ticlopidine, clopidogrel, indometchacin, dipyridamole, omega-3 fatty acids, prostacyclin, nitric oxide, inducers of nitric oxide, inducers of nitric oxide synthase, matrix metalloproteinases inhibitors (MMPIs, TIMPs), anti-GPIIb/IIIa agents, anti-□v□3 agents, anti-□2□1 agents, anti-CD36 agents, anti-GPVI agents, aurintricarboxylic acid, thrombin receptor antagonists, thromboxane receptor antagonists, streptokinase, urokinase, tissue plasminogen activator (WA).

In addition, it is known that platelets that have been cooled below their membrane phase transition temperature (i.e., <15 degrees C. become irreversibly activated. Although the platelets function normally if transfused into a patient, the platelets are rapidly cleared from the body (i.e., in approximately 24 hours, in contrast to normal circulating platelet life span of 7 to 10 days). Although these platelets are cleared rapidly, they bind with high avidity to immobilized VWF. Therefore, transfusion of cooled platelets provides an additional means to enhance thrombus formation at the target site. Therefore, one embodiment of the invention includes controlling platelet-mediated occlusion by administering platelets cooled as noted above.

As noted above, the targeting moiety may be, or may be bound to, one member of a binding pair. Methods according to the invention may require a time period sufficient for accumulation of the targeting moiety at the site of localization, for optimal target to non-target accumulation, for accumulation and binding of the second member of the binding pair, and/or for clearance of unbound substances.

In accordance with the invention, two, three or more step targeting or localization steps may be used. Many of these protocols are well known in the art (see, for example, U.S. Pat. No. 5,578,287 using a biotin/avidin protocol). Exemplary multiple step protocols include, but are not limited to, administering a binding agent-ligand, administering an anti-ligand to clear unbound binding agent and to localize bound binding agent-ligand, and administering an active agent-ligand. As used herein, active agent refers to any therapeutic agent that is active or becomes active and leads to a therapeutic benefit.

In accordance with a method of the invention, the binding agent must be capable of binding a ligand/receptor complex, and may be administered to the patient by any immunologically suitable route. The immune perspective of cancer differs somewhat from the perspective centered on the cancer cell itself. The presence of tumor in a host logically demonstrates that the immune system and its ability to acquire new, useful immunity either is generally damaged or has become specifically tolerant. Insofar as the primary tumor bulk has a negative effect on the immune system, its removal can be considered to have immunotherapeutic potential.

The present invention in combination with immunotherapy may enhance immunologic memory, targeting immunogenic proteins involved in malignant transformation, we may be able to prevent relapse, which is one of the major problems in the long term survival of cancer patients.

For example, the binding agent may be introduced into the patient by an intravenous, intra-arterial, subcutaneous, intraperitoneal, intrathecal, intravesical, intradermal, intramuscular, or intralymphatic route. The composition may be in solid, solution, tablet, aerosol, or multi-phase formulation forms. Liposomes, long-circulating liposomes, immunoliposomes, biodegradable microspheres, micelles, or the like may also be used as a carrier, vehicle, or delivery system. Further more, using ex vivo procedures well known in the art, blood, plasma or serum may be removed from the patient; optionally, it may be desirable to purify the antigen in the patient's blood; the blood or serum may then be mixed with a composition that includes a binding agent or the solid-phase agent according to the invention; and the treated blood or serum is returned to the patient. The clinician may compare the responses associated with these different routes in determining the most effective route of administration. The invention should not be limited to any particular method of introducing the binding agent into the patient.

Administration may be once, more than once, or over a prolonged period. Administration may be made in combination with, serially or alongside, two or more therapies. Administration may be made in combination with two or more therapies once, more than once, or over a prolonged period. As the compositions of this invention may be used for patients in a serious disease state, i.e., life-threatening or potentially life-threatening, excesses of the solid-phase agent may be administered if desirable. Actual methods and protocols for administering pharmaceutical compositions, including dilution techniques for injections of the present compositions, are well known or will be apparent to one skilled in the art. Some of these methods and protocols are described in Remington's Pharmaceutical Science, Mack Publishing Co. (1982).

A solid-phase agent may be administered in combination with other binding agents or may be administered in combination with other treatment protocols or agents, e.g., chemotherapeutic agents, embolizing agents such as Gelfoam or polyvinyl alcohol (PVA) particles or the like.

As is well known in the art, a disadvantage associated with administering treatment agents or treatment agent conjugates in vivo includes non-target or undesirable target binding. It is therefore a desirable attribute of any administered composition to minimize non-target binding, to minimize nontarget exposure to the treatment agent or active agent, and/or to maximize clearance of non-bound binding agent, ligand, or active agent. Moreover, optimizing these attributes typically permits administering a higher dose of active agent, a therapeutic agent, or an element of the process that activates a previously un-activated agent. Those skilled in the art are well versed in selecting the optimal parameters for administering the highest possible dose while remaining safely below a toxic threshold.

In accordance with a preferred embodiment of the invention, therefore, un-activated platelets accumulate or are induced to accumulate at a pre-determined site through binding to the solid-phase agent, and then the properly localized platelets are selectively activated.

In accordance with a preferred embodiment of the invention, activated platelets accumulate or are induced to accumulate at a pre-determined site through binding to the solid-phase agent or through platelets bound to the solid-phase agent.

The effectiveness of the present invention may be monitored by conventional assays that determine thrombus formation, morphometric studies of thrombus formation, tumor necrosis, tumor size, tumor morphology, and/or thrombus formation that results in tumor necrosis, blood flow studies (e.g., angiograph, Doppler ultrasound, radiography, CT scan, MRI), or reduction in pain symptoms. One skilled in the art will recognize that other tests may be performed to assess or monitor therapeutic benefit.

Since some binding agents such as proteins are by themselves poor immunogens, their immunogenicity may be augmented by administration in immunological adjuvants and antigen delivery systems. The immunogenicity of a specific composition may also be increased or optimized by choice of delivery route. For example, the immunogenicity of compositions produced in accordance with the present invention that include a monoclonal antibody may be increased by choosing a mode of delivery that increases the direct contact between the binding agent and the antigen. The referred route is intravenous. Those skilled in the art are conversant with the various choices available, and why one route might be chosen over another route for a particular binding agent.

One skilled in the art will also recognize that liposomes, nanospheres, micelles, or microspheres may be used to administer a composition, and that such administration may result in a therapeutically desirable benefit.

It will be recognized by those skilled in the art that for certain congenital and pathological conditions, some of which are listed below, it is desirable to modify a composition or method of the present invention to compensate for a predisposition of the patient to bleed excessively or to thrombose. Under these circumstances, use of modifying agents, which either enhance or Under these circumstances, use of modifying agents, which either enhance or dampen a method or composition of the invention, can be employed. The use of these modifying agents is predicted to minimize bleeding or clotting episodes. Moreover the use of modifying agents enables controlled administration of a composition according to the invention under normal circumstances (i.e., normal hemostasis).

Exemplary pro-thrombotic or pro-coagulant conditions that may warrant the using of controllers, retarders, or agents that diminish a method or composition of the invention include, but are not limited to, Factor $V^{Leiden}$ deficiency, antiphospholipid syndrome (APS), Protein C and/or Protein S and/or Antithrombin III deficiency, deep vein thrombosis (DVT), pseudo-von Willebrand's disease, Type IIb von Willebrand's disease, peripheral vascular disease (PVD), and high blood pressure, among others. Exemplary conditions that include a risk of hemorrhage that may warrant using enhancers or agents that augment a method or composition of the invention include but are not limited to, any condition that includes a risk of hemorrhage, including but not limited to coagulation factor deficiencies, hemophilia, thrombocytopenia, and anticoagulation therapy, among others. Controlling thrombus generation includes at least one of altering the temperature at the predetermined site, altering the rate of blood flow at the pre-determined site, and altering the blood pressure at the pre-determined site.

As an example of the foregoing, it will be recognized by those skilled in the art that upon initiation of the vascular occlusion process, reversal or dampening of the associated prothrombotic condition may be necessary. In such cases, administration of agents that reduce platelet reactivity will, in turn, reduce response to the vascular occlusion initiators. Such agents are readily known by those skilled in the art and include, but are not limited to: aspirin or aspirin-like compounds, ibuprofen, acetaminophen, ketoprofen, ticlopidine, clopidogrel, indomethacin, omega-3 fatty acids, prostacyclin, nitric oxide, inducers of nitric oxide, inducers of nitric oxide synthase, matrix metalloproteinase inhibitors (MMPIs, TIMPs), anti-GPIb agents, anti-GPIb/IIIa agents, anti-$\alpha v \beta 3$ agents, anti-$\alpha 2\beta 1$ agents, anti-CD36 agents, aurintricarboxylic acid, thrombin receptor antagonists, thromboxane receptor antagonists, streptokinase, urokinase, tissue plasminogen activator (tPA).

An exemplary process in which it may be desirable to enhance or augment platelet occlusion process includes thrombocytopenic (low platelet count) patients. These individuals would benefit from concomitant or pre-administration (transfusion) of platelet products to provide an adequate resource of platelets to accomplish platelet occlusion. It will be recognized by those skilled in the art that all transfusable products mimicking or approximating normal platelet function can be used under such circumstances. Such agents include but are not limited to: random donor platelets, apheresis platelets, autologous platelets, washed platelets, platelet membrane fractions, cooled platelets, frozen platelets, particles containing or expressing platelet membrane components, platelet substitutes and whole blood.

As a further example, specific platelet-function enhancing agents can be employed to boost or enhance initial platelet reactivity once targeted to the site of therapy. Agents known to those skilled in the art have been demonstrated to enhance existing platelet reactivity and/or lower the threshold limiting sufficient platelet reactivity to facilitate irreversible platelet adhesion and/or platelet degranulation and/or platelet/platelet binding and/or platelet accretion about an existing thrombus. These agents include but are not limited to- ristocetin, thrombin, heparin-induced thrombocytopenia (HIT) antibodies or portions thereof, antiphospholipid antibodies (APA) or portions thereof, whole antibody molecules via an Fc-mediated mechanism, anti-ligand-induced binding site (anti-LIBS) antibodies or portions thereof, anti-CD9 antibodies or portions thereof, epinephrine, thrombin receptor activating peptide (TRAP), PAR agonists, cathepsin G. elastase, arachidonate, thromboxane A2 (TxA2) mimetics, TxA2, phospholipase A2 (PLA2), activators of protein kinase C (PKC), adenosine diphosphate (ADP), collagen, von Willebrand factor (VWF), matrix metalloproteinases (MMPs), heparin, heparan sulfate, chondroitin sulfate, ionophores, platelet microparticles, platelet membrane fractions.

Once introduced into the bloodstream of an animal bearing a tumor, hyperplastic tissue, AV-malformation, aneurysm or endoleak, the solid-phase agent will localize in the target vasculature; bind or immobilize platelets, whereby immobilization activates the platelets; and the activated platelets in turn bind and activate other platelets until an occlusion is formed. Platelet activation and binding facilitates leukocyte binding to the activated platelets further enhancing occlusion of the target vasculature.

EXAMPLE 1

Each vial of VWF-coated macroaggregated albumin particles (MAA/VWF) contains 5.0 mL of the particulate suspension, which consists of 4.5 to 7 million particles of the MAA/VWF conjugate in an isotonnic vehicle. The human serum protein content per vial ranges from 5 to 15 mg. By light microscopy, more than 90% of the MAA/VWF conjugate particles are 10-150 µm in diameter and less than 10% are less than 10 µm in diameter.

Summary of the MAA/VWF Particle In Vitro Studies

Mixing MAA/VWF particles with either platelet rich plasma or whole blood in vitro resulted in platelet activation and subsequently platelet aggregation, MAA/VWF particles manufactured with a wide range of ratios of VWF to MAA (by weight) was studied for its ability to cause platelet activation and was found effective over the entire range of ratios studied (1:1 to 1:80). The distribution of VWF on MAA particles was also investigated over the same range of ratios of VWF and MAA, and von Willebrand Factor was found to be uniformly distributed over the MAA particulate surfaces.

Summary of the MAA/VWF Particle In Vivo Studies

The effects of MAA/VWF particles on renal blood flow were evaluated in vivo in a porcine renal infarct model. Administration of MAA/VWF particles by transcatheter arterial injection into the arterial network of the porcine kidney had the following effects:

1. In an acute study in pigs, blood flowing through the kidney decreased over a 20 minute period to less than 20% of the baseline rate (20 mL/minute versus 100 mL/minute).
2. In a chronic study of pigs monitored over a seven day period after treatment with MAA/VWF particles:
a. The blood flow rates to the target kidneys were maintained at less than 10% of the baseline rate (3-5 mL/min);
b. The animals treated with MAA/VWF particles did not develop any adverse events during the observation period.
3. Inspection of the renal vasculature grossly and histologically after surgical removal of the affected organ (acute treatment) demonstrated thrombus formation distal to the angiocatheter down to the level of the capillary beds.
4. Histological examination of the target kidney seven days (chronic study) after treatment showed no evidence of necrosis.

Histological examination of normal tissue from acute (90 minutes) and chronic studies (7 days) showed no sign of thrombosis, indicating that the MAA/VWF particles were completely retained in the capillary beds of the porcine kidneys.

In further studies of MAA/AWF particles to evaluate the agent in acute porcine infarct models, MAA/VWF particles were used to block the blood flow to the porcine spleen, kidneys or lobes of the liver. Sequential small doses of MAA/VWF particles (0.1 mL) were administered by transcatheter arterial injection into the major artery supplying each organ. (Each dose of MAA/VWF particles was followed by 0.1 mL of human platelet rich plasma.) The MAA/VWF particles induced a rapid and sustained reduction in blood flow to each of the targeted organs. No evidence was found of induction of thrombosis in any other organ or tissue of the test animals. No adverse effects of treatment were noted by observation of the living animals.

Summary of the MAA/VWF Particles Biodistribution Studies

Following transcatheter arterial injection of technetium-99m labelled MAA/VWF particles into the arterial network of the porcine kidney or liver, the agent was virtually completely retained within target, organ. The data clearly demonstrate that negligible amounts of radioactivity reached the systemic circulation, and the near background levels of radioactivity in other organs may be attributed to the presence of free pertechnetate and to the metabolic products of the radiolabelled MAA/VWF particles in the blood.

Although the present invention has been described in terms of particular preferred embodiments, it is not limited to those embodiments. Alternative embodiments, examples, and modifications, which would still be encompassed by the invention, may be made by those skilled in the art, particularly in light of the foregoing teachings.

EXAMPLE 2

Advanced renal cancers including renal cell carcinoma and angiomyolipoma can be treated by embolization prior to surgical resection. MAA/VWF particles or particles coated with a similar platelet capture agent can be used as embolic agents to induce a thromboembolus in the arterial supply of advanced renal tumors. A standard embolization procedure would be performed prior to surgical removal of the affected kidney. Prior to the embolic procedures, patients would undergo renal imaging by computerized tomography (CT), magnetic resonance imaging (MRI) or ultrasound to delineate the extent of disease and to measure the tumor masses. Scintigraphic imaging of the metabolic status of the patient's tumor masses would also be performed with F-18 fluorodeoxy-glucose (FDG), and at the discretion of the physician, a baseline study of hypoxic imaging of the abdomen could be performed by means of F-18 misonidazole.

Following selective and global angiography to delineate the renal vasculature, thromboembolization of the renal tumor arterial network would be performed with MAA/VWF particles or particles coated with a similar platelet capture agent such as collagen-coated particles. Treatment with MAA/VWF particles would begin with a starting dose of approximately 1.0 mL ($1\times10^6$ particles) administered intraarterially; additional 1.0 mL doses of MAA/VWF particles would be administered as required to achieve blockage of the blood supply to the tumor mass. Obstruction of target arteries would be assessed by injection of contrast agent after injection of the dose of MAA/VWF particles. Following the procedure, supportive therapy would be given to the patient as required to ameliorate the effects of the post-embolization syndrome (pain, nausea, fever).

In the interval between the embolization procedure and the complete or partial nephrectomy scintigraphic imaging of the chest may be repeated with FDG. At the discretion of the physician, scintigraphy with F-18 misonidazole may also be repeated.

Safety laboratory studies could be performed pretreatment, daily for the first week after the embolization procedure (Days 2-7), every other day for the second week (Day 8, 10 and 12), weekly for the remainder of the first month (Days 15, 22, and 29), and biweekly for the second month (Days 43 and 57).

During the second and fifth weeks post-operatively (Study Days 8-12 and Days 29-33), the patient could have a CT examination of the abdomen performed to evaluate the patient's status post-surgery and to evaluate the patency of the residual renal arterial vasculature (if any). At this time and at the discretion of the physician, scintigraphic imaging may be repeated with FDG and/or F-18 misonidazole.

EXAMPLE 3

Patients with primary hepatocellular carcinoma (HCC) who are candidates for standard embolotherapeutic procedures were treated with MAA/VWF particles to induce embolization of target vasculature feeding the tumors. Patients were imaged by triphasic CT to delineate the extent of disease and to measure the size of index tumor lesions.

Following selective catheterization of the right or left hepatic artery using a percutaneous femoral artery approach a suitable dose of Technetium Tc-99m Albumin Aggregated Injection (Tc-99m MAA) was injected through the catheter. Scintigraphic imaging confirmed the absence of arterial shunts that might result in untoward arterial embolization.

Following selective and global angiography to delineate the liver vasculature, the patients were treated by means of the standard protocol for transcatheter arterial chemoembolization (TACE). Doxorubicin (75 mg/m$^2$) was emulsified in 10 mL of Lipiodol® and infused in accordance with standard procedures, while the subsequent embolization of the arteries feeding the tumors was performed with MAA/VWF particles.

Embolization of the target hepatic artery branch(es) with MAA/VWF particles began with a starting dose of approximately 1.0 mL (approximately $1\times10^6$ VWF-MAA particles) which was injected by transcatheter arterial injection. Additional 1.0 mL doses of MAA/VWF particles were administered as required until blockage of the target arteries was achieved. Obstruction of target arteries was assessed by injection of contrast agent 2 minutes after injection of the dose of MAA/VWF particles.

Following the chemoembolization procedure, symptomatic therapy was given as required to ameliorate the effects of the post-embolization syndrome (pain, nausea, fever).

The patients were re-imaged at one and four weeks after the procedure by CT, and then in accordance with standard medical care, every 3 months by CT and/or ultrasound. Long term follow up involved standard patterns of care with time to disease progression and patient survival data obtained by chart review.

EXAMPLE 4

HCC patients treated by TACE as outlined in Example 3 using MAA/VWF as the embolic agent were assessed by CT to determine the affect of therapy on index tumor lesions. Five patients were treated with MAA/VWF in combination with doxorubicin and Lipiodol®. No serious adverse events were attributed to the administration of MAA/VWF particles. Four of the five patients treated with MAA/VWF particles showed tumor regression ranging from approximately 8% to 27% decrease in tumor volume (response measured 5 weeks after treatment). The remaining patient showed an increase in tumor size amounting to 2% (by volume). All responses fell into the "stable disease" category. One patient received a liver transplant after TACE using MAA/VWF particles as an embolic agent.

We claim:

1. A method for treating a disease or condition, comprising non-systemically administering to a mammal at a pre-determined site and having a disease or condition a solid-phase agent comprising a binding agent capable of binding platelets, said solid-phase agent being greater than about 1 micron in size, and subsequently inducing a thrombus in vivo at or near said site, comprising:
    capturing platelets by binding the platelets to the platelet binding agent immobilized on or within the solid-phase agent,
    inducing activation of the platelets, and
    allowing a thrombus to form; thereby providing a beneficial result in treating said disease or condition; and
    administering at least one other therapy, thereby providing a beneficial result in treating said disease or condition, wherein said disease or condition is selected from the group consisting of hepatocellular carcinoma (HCC), renal cell carcinoma (RCC), hemorrhagic stroke, saphenous vein side branches in saphenous bypass graft surgery, aortic aneurysm, vascular malformations, and solid tumors; embolization of tumor vasculature prior to organ transplantation, and embolization of vasculature prior to tissue or organ resection; any pathological condition where blood is involved or present, comprising cancer, hyperplastic cells, excessive bleeding or arteriovenous (AV) malformations, or which are hemorrhaging; solid hyperplastic tissue; cancer pain, uterine fibroids, pelvic congestion, menorrhagia, varicoceles, hemoptysis, aneurysms, visceral artery aneurysms, pseudoaneurvsms and endoleaks; peripheral vascular disease (PVD), and high blood pressure; and any condition that includes a risk of hemorrhage, including but not limited to coagulation factor deficiencies, and hemophilia.

2. A method of treating a vascularized tumor or hyperplastic tissue comprising non-systemically administering to a pre-determined site at or near a vascularized tumor or hyperplastic tissue von Willebrand Factor bound to a solid support, said solid support being greater than about 1 micron in size; allowing the von Willebrand Factor to capture and activate platelets, allowing the activated platelets to form a thrombus; and administering at least one additional therapeutic agent or protocol.

3. The method of claim 2 wherein administering comprises administering using a catheter, microcatheter, needle, syringe, by a surgical procedure, or by manual placement.

4. The method of claim 1 wherein administering comprises administering in combination with one or more therapies once, more than once, or over a prolonged period.

5. The method of claim 4 wherein administering comprises administering in combination with serially or alongside one or more therapies.

6. The method of claim 1 wherein said disease or condition comprises vascularized tumor or hyperplastic tissue.

7. The method of claim 1 wherein at least one other therapy comprises any medical, pharmaceutical, and/or biological therapy.

8. The method of claim 1 wherein the solid phase agent comprises macroaggregated albumin particles.

9. The method of claim 8 wherein the platelet binding agent comprises VWF or collagen.

10. The method of claim 1 wherein the platelet binding agent comprises VWF or collagen.

11. The method of claim 1 wherein the solid phase agent further comprises a targeting agent for binding the solid phase agent to a selected site, and administering said solid phase agent non-systemically.

12. The method of claim 11 wherein said selected site is in the venous system.

13. The method of claim 12 wherein the selected site is the vasculature of the venous system.

14. The method of claim 1 wherein the other therapy is selected from the group comprising: chemotherapy, chemoembolization, radiofrequency ablation, microwave treatment, cryoablation, percutaneous ethanol injection, resection, transplantation, angiogenesis inhibitors, immunotherapy, tyrosine kinase inhibitors, interferon, internal radiation, external radiation, cytostatic agents, gene therapy, embolic agents, hormone therapies, and growth factor receptor inhibitors.

15. The method of claim 1 wherein administering includes the use of a stent or coil.

* * * * *